United States Patent
Henry

[11] 4,041,091
[45] Aug. 9, 1977

[54] FRACTIONATION OF AROMATIC STREAMS

[75] Inventor: Michel Jacques Henry, Brussels, Belgium

[73] Assignee: UOP Inc., Des Plaines, Ill.

[21] Appl. No.: 659,393

[22] Filed: Feb. 19, 1976

[51] Int. Cl.$^2$ .............................................. C07C 3/62
[52] U.S. Cl. .................................. 260/672 T; 203/25; 208/95
[58] Field of Search ...................... 260/672 T; 208/95

[56] References Cited

U.S. PATENT DOCUMENTS

| | | | |
|---|---|---|---|
| 3,304,340 | 2/1967 | Noll | 260/672 |
| 3,701,813 | 10/1972 | Stenmark | 260/668 A |
| 3,784,621 | 1/1974 | Suggitt | 260/672 T |

Primary Examiner—Delbert E. Gantz
Assistant Examiner—G. E. Schmitkons
Attorney, Agent, or Firm—James R. Hoatson, Jr.; Richard D. Stone; William H. Page, II

[57] ABSTRACT

A fractionation scheme applicable to a transalkylation process in which an admixture of toluene and $C_9$ alkylbenzene is converted to benzene and $C_8$ alkylbenzene is disclosed. Transalkylation zone effluent containing $C_6$ to $C_{10}+$ alkylbenzene is passed into a fractionation zone wherein an admixture of benzene and toluene is withdrawn as a lower boiling fraction, and $C_8+$ alkylbenzenes are withdrawn in admixture as a higher boiling fraction. The benzene and toluene fraction is introduced into a fractionator and separated therein. The $C_8+$ fraction is fractionated into xylenes and $C_9+$. The $C_9+$ fraction is fractionated into a $C_9/C_{10}$ overhead fraction and $C_{10}+$ bottoms fraction. Toluene and $C_9/C_{10}$ are then fed to the transalkylation zone. Significant savings in utilities are realized by using a xylene vapor fraction to reboil the column fractionating transalkylation zone effluent, and by using the $C_9/C_{10}$ vapor fraction to reboil the column fractionating benzene and toluene.

5 Claims, 1 Drawing Figure

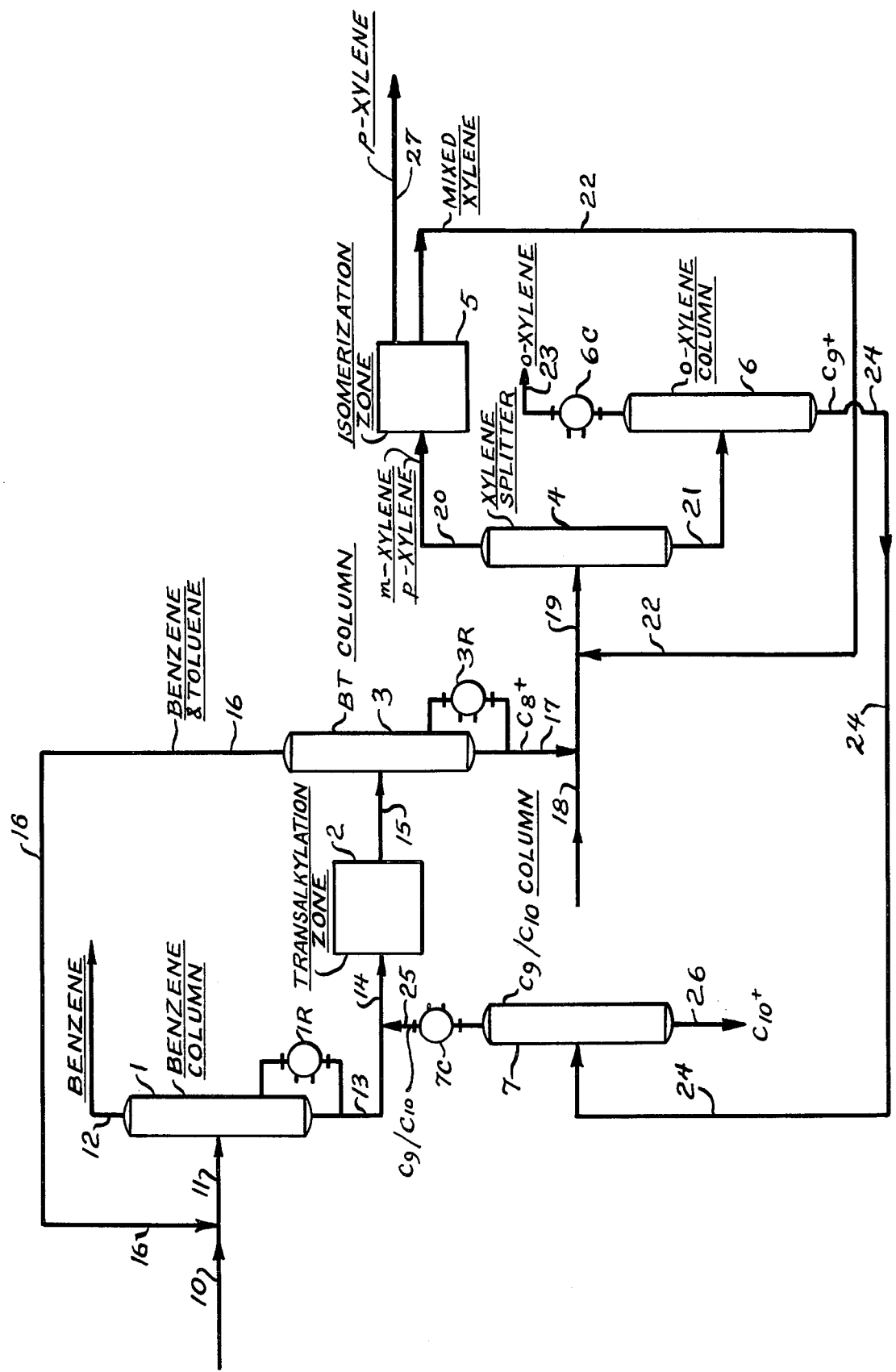

FRACTIONATION OF AROMATIC STREAMS

BACKGROUND OF THE INVENTION

The present invention relates to a process in which an admixture of toluene and C$_9$ alkylbenzene is transalkylated to form benzene and C$_8$ alkylbenzene. It specifically relates to fractionation of the reaction zone effluent of a process in which an admixture of toluene and C$_9$ alkylbenzene is transalkylated to benzene and C$_8$ alkylbenzene.

At the present time, about 90 percent of the benzene produced in the U.S. is derived from petroleum sources and the balance is derived from natural gas and coal. This represents a sharp change from as recently as 1957 when the steel and coal industries produced more benzene than did the petrochemical industry. This is in large part due to the high growth rate of benzene demand experienced during the past decade, averaging 12 percent per year during that time, but also reflects a stagnation of benzene production by tar distillers and coke oven operators. About 85 percent of benzene consumption in the U.S. now goes to production of ethylbenzene, phenol, and cyclohexane, while a relatively small amount goes to anilin, maleic anhydride, chlorobenzene and other uses. Ethylbenzene, which consumes 48% of U.S. benzene production, is an intermediate chemical in the production of styrene-butadiene rubber and styrene resins such as polystyrene, both the straight and rubber-modified polystyrenes finding application in consumer products such as packaging, toys, luggage, housewares, etc. About 20% of benzene production is used to prepare phenol, which is produced by various methods, principally by way of cumene as an intermediate, and is itself an intermediate chemical in the production of phenolic resins, which are used in molding applications, polywood bonding, laminating resins, friction materials, thermal insulation, etc. About 17% of benzene production goes to produce cyclohexane, an intermediate in the manufacture of nylon. Because of benzene's use in the production of consumer goods, it is expected that demand will continue strong, but perhaps not at the annual growth rate of 12 percent experienced during the past decade due to benzene's present unit cost more or less quadruple that of the previous decade.

Like benzene, demand for xylene has been strong principally due to increasing demand for paraxylene. Over the past decade, while yearly production of mixed xylene has increased 9 percent, that of orthoxylene has increased 13 percent and that of paraxylene has increased 24 percent. Xylenes are produced almost solely from petroleum with less than 2 percent production from coal tar and coke oven light tars. Xylene isomers together with ethylbenzene as produced from petroleum are normally found as follows as related to the total C$_8$ aromatics: ethylbenzene 15–25 percent, orthoxylene 15–25 percent, metaxylene 35–45 percent, and paraxylene 12–22 percent. As stated hereinabove, ethylbenzene is used in the production of styrene; orthoxylene is a feedstock in the production of phthalic anhydride while paraxylene is used for polyester manufacture.

Benzene, ethylbenzene, and the xylene isomers are principally prepared and separated together with toluene from petroleum by a series of processing units as follows: (1) In a crude unit, crude petroleum is fractionated into several boiling range cuts, one of which is a naphtha cut which boils in the range of about 100° to 350° F. (2) After depantanizing or deisohexanizing of the naphtha, it is passed to a desulfurization and reforming unit, where sulfur is removed to less than one part per million and the aromatic precursors in the naphtha are upgraded to their respective aromatics. (3) Reforming unit effluent, normally containing about 30 to 60 percent aromatics, is passed into an aromatics extraction unit, wherein normally either a glycol or Sulfolane is utilized as a solvent to extract aromatic components from non-aromatic ones. Extract containing about 99.9 percent aromatics is clay treated to reduce olefin content and is separated in a fractionation zone to prepare the various aromatic components in purified streams as desired. Several important variables affect the quantity of individual aromatic products obtained by the hereinabove processing scheme, the most important of them being the quality of the crude and the market for products. Crudes vary significantly in quality in regard to aromatic and aromatic precursors content, and in regard to the ratio of aromatics and aromatic precursors by carbon number. While there is significant variation, benzene, toluene and xylene (including ethylbenzene) are typically produced in the following ratio:

benzene = 1
toluene = 2.5 to 3.0
xylene and ethylbenzene = 2.0 to 2.5

Although it appears that the production rates of toluene and xylene may be greater than that of benzene, actual benzene, toluene, and xylene U.S. production in 1973 were 1453, 936, and 818 million gallons, respectively. Consumption is far greater of benzene than toluene or xylene, and accordingly, production of toluene and xylene is restricted, normally by one of two means. Firstly, a naphtha cut with an end point of about 230°–300° F may be processed, thereby substantially reducing the toluene and xylene precursors in the reforming unit feedstock; and secondly, a dealkylation unit may be utilized to convert toluene to benzene. A further explanation of higher benzene production than toluene or xylene is related to the aromatics production from coke-oven light oils, coal tar, and pyrolysis processes, which is similar from these sources in distribution of benzene, toluene, and xylene produced. While there may be substantial variation from one producer to another, benzene, toluene and xylene comprise about 80, 15 and 5 percent, respectively, of the BTX aromatics produced in these processes.

Toluene, unlike benzene, orthoxylene, and paraxylene, does not have strong demand as an intermediate chemical in the manufacture of consumer products. End uses such as polyurethane production, aviation gasoline, or solvents require only about 35 percent of U.S. production; the remainder of U.S. toluene production is dealkylated to benzene. In the present description, U.S. production of aromatics stated hereinabove is the production and separation into relatively purified streams of said aromatics, but in fact, total production is substantially greater. For example, only about 20 percent of total toluene produced is actually separated into a purified stream, the remainder being used as a high octane gasoline blending component. As a blending component, toluene has a premium value with a research octane number of 105.8. With the present emphasis on lead-free gasoline, high octane blending components such as toluene are becoming relatively more valuable than previously, but toluene dealkylation has increased and now accounts for about 32 percent of benzene production as compared to about 22 percent in 1965. Accordingly, it is observed that toluene dealkylation is becoming an increasingly attractive route to benzene production.

Both thermal and catalytic toluene dealkylation processes are available to produce benzene. Both catalytic and thermal dealkylation are practiced in the presence of hydrogen at high reaction temperatures to about 1200°–1300° F to achieve over 95 percent dealkylation to benzene. Both processes may accept feedstock including alkylaromatics higher than toluene, and these are also normally converted to benzene although mild conversion of $C_9$ and heavier aromatics to xylene is known in the art. Feedstocks including paraffins, naphthenes, and aromatics are also provided to both dealkylation processes to result in benzene and light paraffin products, i.e., methane and ethane. Because of high hydrogen consumption and low benzene volume yields, dealkylation to benzene of alkylaromatics heavier than toluene is not advantageous as toluene dealkylation.

A relatively new process development is a catalytic transalkylation process in which toluene is transalkylated to benzene and xylene in the presence of hydrogen. The process is advantageous as compared with dealkylation processes in the respect that hydrogen consumption is substantially reduced and reaction temperatures are less severe. In a transalkylation process in which toluene is a feedstock, the principal reaction taking place is as follows:

$$2\ C_7H_8 \rightarrow C_6H_6 + C_8H_{10}$$

Molar yields of benzene and xylene are essentially achieved in the process, and while the theoretical volume yield of benzene from toluene is about 84 percent by dealkylation, the combined theoretical volume yields of benzene and xylene is about 100 percent from transalkylation of toluene. Of the $C_8$ aromatic product, only 1 to 2 percent is ethylbenzene, with the xylene isomers comprising the remainder in the following proportions: para 23–25 percent, meta 50–55 percent and ortho 23–25 percent.

In addition to benzene and $C_8$ aromatic products, about 2 to 4 percent of the reactant is converted to light hydrocarbons, such as methane and ethane, and heavy aromatics containing 10 or more carbon atoms. An alkylaromatic product containing 9 carbon atoms is produced in the reaction, but following separation of the reaction zone effluent, it may be recycled to extinction in the reaction zone. Although the primary reactant introduced into the process is toluene, $C_9$ aromatic may also be used and upgraded principally to xylene and a $C_{10}$ aromatic. For example, trimethylbenzene is principally converted to xylene and tetramethylbenzene.

The process of the present invention is applicable to a transalkylation process in which an admixture of toluene and $C_9$ alkylbenzene is transalkylated in a reaction zone wherein complete conversion of the reactants is not achieved, thus requiring separation and recycling to the reaction zone of unreacted reactants.

An object of the present invention is to provide an improved process in which toluene and $C_9$ alkylbenzenes are transalkylated to provide benzene and xylene product.

A specific object of the invention is to reduce energy consumption in a transalkylation process to convert toluene and $C_9$ alkylbenzenes to benzene and xylene.

Accordingly, the present invention provides a combination xylene separation and a toluene transalkylation process, for producing benzene and orthoxylene comprising the steps of: (a) transalkylating a mixture of toluene and $C_9$ alkylbenzene in a transalkylation zone at transalkylation conditions to produce a transalkylation zone effluent comprising benzene, toluene, $C_8$ alkylbenzenes, $C_9$ alkylbenzenes, and $C_{10}$ alkylbenzenes; (b) fractionating at least a portion of said transalkylation zone effluent in a distillation column wherein benzene and toluene are recovered as an overhead fraction and materials heavier than toluene are recovered as a bottoms fraction; (c) fractionating said benzene and toluene fraction in a fractionation column to produce a benzene product and to recover a toluene-rich stream which comprises at least a portion of the charge to the transalkylation zone; (d) passing at least a portion of said bottoms fraction, comprising material heavier than toluene, into a xylene fractionator, and recovering overhead a stream comprising orthoxylene and recovering as a bottoms fraction a stream comprising $C_9$ and $C_{10}$ alkylbenzenes; (e) passing the $C_9$ and $C_{10}$ alkylbenzene bottoms fraction to a fractionation zone to recover overhead a stream comprising $C_9$ alkylbenzenes, at least a portion of which $C_9$ alkylbenzenes stream is charged to the transalkylation zone; (f) reboiling the column producing benzene product by indirect heat exchange with vapors from the column producing $C_9$ alkylbenzenes as an overhead fraction; and, (g) reboiling the column producing benzene and toluene as an overhead fraction by indirect heat exchange with a stream comprising orthoxylene vapors obtained as an overhead vapor fraction from the xylene fractionator.

In a typical prior art process, the effluent of a toluene transalkylation reaction zone containing benzene, toluene, xylene, $C_9$ aromatics, and aromatic heavier than $C_9$ is separated in a fractionation zone into product and recycle streams each of which contains a high purity single carbon number aromatic component. Benzene, xylene, and aromatics heavier than $C_9$ are withdrawn as product streams, while toluene and $C_9$ aromatics are recycled as two separate purified streams to the transalkylation zone. In the fractionation zone, reaction zone effluent is typically separated to form benzene as the overhead fraction of a first fractionation, toluene as the overhead fraction of a second fractionator, $C_8$ aromatics as the overhead fraction of a third fractionator, $C_9$ aromatics as the overhead fraction and $C_{10}$ aromatics as the bottoms fraction of a fourth fractionator. The bottoms fraction of each column is passed as feed to the next column in the series. Each fractionator is provided with an overhead condensation and reflux system and a bottoms indirect reboiler system known to one skilled in the art.

A significant improvement was made over this prior art process when it was discovered that one column could be eliminated, and much expensive heat exchange equipment eliminated by a modification in the flow scheme. Thus, instead of "peeling" off only the lightest component from a multicomponent mixture a more radical fractionation was attempted. Thus, the first fractionator separated the reaction zone effluent to give BT overhead and $C_8$ to $C_{10}$ + alkylaromatics as a bottoms fraction. The $C_8$ and $C_{10}$ + bottoms are sent to a second fractionator. There a $C_8$ alkylbenzene, orthoxylene, is withdrawn as an overhead product stream while $C_9/C_{10}$ + alkylaromatics are withdrawn as a bottoms fraction. The other $C_8$ aromatic isomers were sent to an isomerization unit. The BT fraction and the $C_9/C_{10}$ + fraction are passed into a third fractionator, at separate loci of the column, and separated into an overhead product stream containing benzene, a sidecut recycle stream containing $C_7$ and $C_9$ aromatics in admixture, and a bottoms product stream containing $C_{10}$ + aromatics. Each fractionator was provided with indirect overhead condensation and indirect bottoms reboiler system known to one skilled in the art. The ortho-xylene product, recovered as an overhead fraction, was used to reboil the fractionator downstream of the transalkylation unit. Benefits of this processing scheme included: (1) elimination of a fourth fractionator including an overhead condensation system and a bottoms reboiler system, and (2) reduction of utility requirement, as $C_9$ vapors provide heat to vaporize benzene for the benzene-toluene split. This flow scheme will be called scheme I, and is not a part of the present invention.

Similarly, the flow scheme wherein peeling of a single pure component from a multicomponent mixture will be called scheme II. Scheme II is also not a part of the present invention.

The present invention will be called scheme III. It is an improvement over both of the prior art schemes in that it permits substantial savings in utility costs when compared to either scheme I or II.

DESCRIPTION OF THE DRAWING

The specific embodiment of the invention depicted in the drawing shows a transalkylation zone and an isomerization zone. These units and their various fractionators are interconnected in a way to result in a significant savings of utility cost. Each separate loop will be discussed in turn.

In the transalkylation circuit, an aromatics feed is charged to a benzene column via lines 10 and 11. Benzene column 1 provides a pure benzene product as an overhead stream in line 12. Heat input required in column 1 is supplied by reboiler 1R. Aromatics heavier than benzene are recovered as a bottoms fraction via line 13 and are charged via line 14 into transalkylation zone 2. Zone 2 effluent in line 15 consists of BTX and heavier aromatics. These materials are separated in fractionator 3, or BT column, into an overhead fraction consisting of benzene and toluene. This overhead fraction is returned via line 16 to benzene column 1. Xylenes and heavier aromatics are recovered from the BT column as a bottoms fraction via line 17. Heat input to the BT column 3 is supplied by reboiler 3R.

The isomerization circuit accepts as a feed stream both xylene-rich from an outside source via line 18 and xylene and heavier materials in line 17 derived from the BT column in the transalkylation circuit. These xylenes and heavier aromatics are charged via line 19 into xylene splitter 4. Meta- and para-xylene or m-X or p-X, are recovered overhead and charged to isomerization zone 5. Zone 5 also includes a facility for the absorptive separation of para-xylene from mixed xylenes. Although absorptive separation is preferred, other para-xylene recovery schemes, e.g., crystallization schemes may also be used. Effluent from the para-xylene separation zone is isomerized to substantially equilibrium composition. Effluent from zone 5, containing mixed xylenes is charged to xylene splitter 4 via lines 22 and 19. Para-xylene is withdrawn from zone 5 by line 27. Ortho-xylene, or o-X, and $C_9$ + aromatics are recovered as a bottoms fraction from xylene splitter 4 via line 21. This stream is charged to ortho-xylene column 6. Ortho-xylene is recovered overhead via line 23. Reflux requirement for the ortho-xylene column 6 is supplied by means not shown in column 6 by ortho-xylene vapor condensed in condenser 6C. $C_9$ + aromatics are recovered from column 6 via line 24. These aromatics are separated into a $C_9$ and $C_{10}$ overhead fraction and a $C_{10}$ + bottoms fraction by $C_9/C_{10}$ column 7. The $C_{10}$ + material is withdrawn via line 26 and used as gasoline blending stock or for other purposes. The overhead fraction, comprising vaporized $C_9$ and $C_{10}$ alkylaromatics, passes through condenser 7C and a portion of the condensate is returned by means not shown as reflux to column 7. The $C_9$ and $C_{10}$ aromatics not required as reflux are charged via lines 25 and 14 into transalkylation zone 2.

The fractionators, pumps, heat exchange equipment, and other details of interconnecting the various reaction zones and fractionators are all well known in the art.

DETAILED DESCRIPTION OF THE INVENTION

Key feature of the present invention is the discovery that by interconnecting the fractionators and reaction zones as shown, and by use of the overhead fraction from column 6 to reboil column 3, and use of the overhead fraction from column 7 to reboil column 1, that a significant savings in utilities can be realized. The magnitude of the savings can best be realized by comparing it to two prior art flow schemes, hereinbefore designated as scheme I and scheme II. Scheme I provided for the combination of columns 1 and 7 into a single column. The advantage of prior art scheme I was that it eliminated heat exchange equipment 1R and 7C. The disadvantage of scheme I was that mixing the $C_9$ + material in line 24 with the relatively pure benzene and toluene material in column 1 seriously degraded the operation of this column. It appears that much of the work done in obtaining a concentrated BT fraction, and concentrated $C_9$ + fraction, was lost by mixing these two streams in a common fractionator. Thus, scheme I resulted in the highest utility cost of any of the studied schemes, even though scheme I would save significantly on capital cost of the unit.

Scheme II is a conventional scheme wherein peeling of one pure component as an overhead fraction a multicomponent mixture occurs successively in several fractionators in series. Such a fractionation scheme may be thought of as an extended version of the BTX fractionation train commonly found downstream of aromatics extraction units. Thus, a first fractionator removes benzene overhead while sending everything remaining into the second fractionator. The second fractionator removes toluene as an overhead fraction, while sending everything remaining into the third fractionator. The third fractionator removes xylenes overhead, while sending $C_9$ + material into yet a fourth fractionator. Such a scheme has an appealing simplicity, and it might be thought that it would result in the lowest utility cost, because it would mean that each product stream would only be refluxed once. Thus, in the first fractionator, or benzene fractionator, benzene is refluxed to the column, and benzene product is withdrawn as a pure stream. If benzene and toluene are both withdrawn as an overhead fraction, the benzene produced still has to be separated from the toluene, and the benzene has to be refluxed a second time in the column separating benzene from toluene. Although this theory, of refluxing only the product, seems reasonable, in practice it produces a significantly higher utility consumption than in the method of the present invention, scheme III. It is only in scheme III, which provides for an unconventional fractionation train, and for an unconventional method of reboiling columns and condensing overhead streams that maximum economy is realized. The vapor fraction from ortho-xylene column 6 provides almost enough heat to supply the total heat input required in BT column 3. Similarly, the overhead vapors from column 7 provide almost enough heat to supply the reboiler heat required in column 1. A small trim reboiler, not shown in the drawing, is required on both column 1 and column 3. These trim reboilers provide process control, permit rapid startup, and add the slight amount of extra heat input required which is not supplied by the respective condensing overhead streams.

This flow scheme is also unusual in that it uses condensing $C_9$ and $C_{10}$ vapors to boil toluene (the material in the bottom of column 1 is primarily toluene), while using condensing $C_8$ vapors to boil material which is also comprised largely of $C_8$ aromatics (the material in the bottom of column 7 consists primarily of xylenes). It would be considered more conventional to use condensing $C_8$'s to boil $C_7$'s and condensing $C_9$'s to boil $C_8$'s. However, such a system would not be optimum because the amount of heat contained in the xylene vapors is much greater than the amount of heat required in benzene column 1, and the amount of heat in the $C_9$ and $C_{10}$ vapors is not nearly enough to boil the material in column 6. It is believed that this relationship will hold true for any unit which combines transalkylation and isomerization as shown and which uses as a primary feed source feed streams derived from catalytic reformate.

Reactants suitable for the present process are toluene alone, $C_9$ alkylbenzene alone, or an admixture of the two.

To effect a transalkylation reaction, the present invention incorporates a transalkylation catalyst, but no limitation is intended in regard to a specific catalyst. One skilled in the art is familiar with several transalkylation catalysts suitable for use in the present invention. For example, in U.S. Pat. No. 3,849,340 a catalytic composite comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of about 12:1 to about 30:1 and a metal component selected from copper, silver, and zirconium is described. Friedel-Crafts metal halides such as aluminum chloride have been employed with good results and are suitable for use in the present process. Hydrogen halides, boron halides, Group I-A metal halides, iron group metal halides, etc., have been found suitable. Refractory inorganic oxides, combined with the above-mentioned and other known catalytic materials have been found useful in transalkylation operations. Crystalline aluminosilicates have also been employed in the art as transalkylation catalysts. Other catalysts including a mordenite component and a metal component selected from a Group VIII metal activator are known in the art.

Transalkylation reactions are preferably effected at a temperature of about 400° to 1000° F. in a continuous manner utilizing a catalyst in a fixed bed. A vapor phase operation, preferably in the presence of hydrogen, is more desirable than a liquid phase operation. Contact time, expressed in terms of liquid hourly space velocity, of about 0.1 to about 20 hours$^{-1}$ or more may be utilized. A pressure of about 1 to 60 atmospheres is recommended to effect transalkylation of alkylbenzenes such as toluene and $C_9$ alkylbenzene. The transalkylation step in the present process may be embodied in a batch type reaction scheme or a continuous type reaction scheme, the latter being preferable. This is effected by employing the transalkylation catalyst as a fixed bed in a reaction zone of the transalkylation zone and continuously charging the reactant stream into the reaction zone, passing the hydrocarbons over the catalyst bed, and withdrawing the converted hydrocarbons from the reaction zone. A large variety of vessels suitable for use as a reactor in a transalkylation reaction zone is well known in the art.

After cooling to about 100° F., the resultant effluent of the transalkylation reactor is passed into a vessel, not shown, and forms a principally hydrogen gas phase and a liquid phase, the former being recycled to the reaction zone, although a portion may also be withdrawn from the process for the purpose of maintaining hydrogen purity in the hydrogen recycle gas stream at a suitable high value, and the latter phase being passed into a stripping column, not shown, wherein light gases including $C_1$–$C_4$ paraffins are stripped from the liquid phase. To accomplish the routine cooling, heating, and separation found in the transalkylation zone, oil or gas fired heaters, indirect heat exchange means, a separation drum, a stripping column, a hydrogen recycle gas, compressor, etc., all known in the art are required. The liquid effluent of the transalkylation zone, stripped of light hydrocarbons, contains $C_6$ to $C_{10}$ alkylbenzenes, including benzene, unreacted toluene, $C_8$ alkylbenzene, unreacted $C_9$ alkylbenzene, and $C_{10}$ alkylbenzene, and also some $C_{10}+$ alkylaromatics.

Toluene and $C_9$ alkylbenzenes suitable as reactants for the present process are commonly prepared as product streams from an aromatics extraction process and its associated fractionation zone. The aromatics extraction process is well known in the art and normally comprises two zones, a liquid-liquid extraction zone, usually referred to as the extraction section, and an extractive distillation section. In the extraction section, a hydrocarbon feedstock normally in a boiling range of about 150 to 350° F. and including about 30–60 percent by volume aromatics and 70–40 percent paraffins and naphthenes is introduced into an extractor wherein the feedstock is contacted with a solvent, normally Sulfolane or a glycol. Two liquid phases, result, the lighter one being a raffinate or principally non-aromatic phase which is withdrawn as a product stream, and a heavier one which is referred to as the rich solvent phase and contains principally aromatic extract and solvent, but also contains non-aromatic hydrocarbon impurities. When Sulfolane is the solvent, extraction conditions include a temperature of about 100° to 300° F., a pressure of about 10 to 30 atmospheres, and a solvent/hydrocarbon feed volumetric ratio of about 1.0 to 6.0. The rich solvent phase is further processed to separate solvent, extract, and non-aromatic components by a combination of extractive distillation and steam stripping operations, at extractive distillation and steam stripping conditions selected to result in a lean solvent relatively free of hydrocarbons and suitable for recycling to the extractor, a non-armatic rich stream suitable for recycling to the extractor, and an extract including at least 99.5 percent $C_6$–$C_{10}$ alkylbenzene. All extraction and distillation equipment is well known in the art, and various process patents describe the extraction and solvent separation steps fully. The following U.S. Patents are useful to the further understanding of the process and equipment used in separating $C_6$–$C_{10}$ alkylaromatics from non-aromatics of the same boiling range by extraction and extractive distillation: U.S. Pat. Nos. 3,435,087, 3,361,664, 3,433,735, 3,466,345, 3,619,419, 3,207,692, 3,338,823, 3,661,771, 2,902,413, and 3,396,101, the teachings of which are incorporated by reference. The extract product of the extraction section is commonly passed into a fractionation section, wherein ordinary distillation techniques are used to separate the $C_6$–$C_{10}$ alkylbenzenes into benzene, toluene, $C_8$ alkylbenzene, $C_9$ alkylbenzene, and heavier fractions. Two of these fractions, the toluene fraction and the $C_9$ alkylbenzene fraction are suitable as reactants in the transalkylation zone of the present process. However, a processor who is producing benzene and xylene products by transalkylation of toluene and $C_9$ alkylbenzene is also likely to be preparing BTX products by an aromatic extraction process, and accordingly, it is beneficial to combine the fractionation zones of the aromatics extraction process and the transalkylation process by admixing extract effluent of the aromatics extraction process and the liquid effluent from the transalkylation zone, and passing the admixture into a single fractionation zone. In this case, no fresh reactants need be introduced into the transalkylation zone except those which are introduced into the fractionation zone of the present process in the extract stream from the aromatics extraction zone, separated in the fractionation zone, and recycled to the transalkylation zone as described hereinbelow.

In conventional practice, various feed or product streams of fractionation columns are clay treated to reduce olefin content of the aromatic products to an acceptable level. Treatment is effected by passing a stream at a temperature of about 300° to 500° F. and sufficient pressure to maintain a liquid phase, about 15 to 40 atmospheres, over a suitable natural clay at a liquid hourly space velocity of about 0.4 to 5.0 hour$^{-1}$.

The benzene product fraction is described as being withdrawn as an overhead fraction from the benzene fractionator, however, it is within the scope of this invention to withdraw the benzene fraction as a sidecut liquid stream from 1 to 10 trays below the top tray of the third fractionator, preferably at about the fifth tray below the top tray.

Operating pressure in the fractionators is about 1 to 5 atmospheres, with operating temperatures corresponding to the pressure and fluid composite. Sufficient heat is introduced into the reboiler of each column to result in a reflux/feed molar ratio of about 1/1 to 4/1, about 1.4/1 to 2/1 being preferred, with only the upper feed to the third fractionator considered in application of the stated molar reflux/feed ratio.

ILLUSTRATIVE EMBODIMENT

| SCHEME I | External Reflux Ratio | Actual Trays | Column Diameter (Meters) |
|---|---|---|---|
| *B + $C_9$/$C_{10}$ Column | 1.7 | 129 | 3.9 |
| BT Column | 1.2 | 50 | 4.5 |
| O-X Column | 2.8 | 100 | 3.5 |
| SCHEME II | | | |
| B Column | 1.2 | 54 | 3.5 |
| T | 1.0 | 50 | 3.7 |
| O-X | 2.4 | 80 | 3.0 |
| $C_9$/$C_{10}$ | 1.5 | 50 | 2.6 |
| SCHEME III | | | |
| B | 1.2 | 54 | 3.2 |
| BT | 1.2 | 50 | 4.5 |
| O-X | 2.8 | 100 | 3.5 |
| $C_9$/$C_{10}$ | 1.5 | 50 | 2.6 |

*In Scheme I, These Two Columns Are Combined Into One

HEAT TRANSFER STREAMS

| SCHEME III | Flow, M lbs/hr | ° F. | Heat Transfer MM Btu/Hr |
|---|---|---|---|
| B Reboiler | 700 | 283 | 34.6 |
| $C_9$/$C_{10}$ Condenser | 204 | 380 | 31.4 |
| BT Reboiler | 436 | 356 | 46.1 |
| O-X Condenser | 290 | 385 | 44.2 |

NET HEAT COMPARISON

|  |  | MM Btu/Hr |  | % Of Scheme III |
|---|---|---|---|---|
| Scheme I | = | 59.46 | = | 133.2 |
| Scheme II | = | 54.94 | = | 123.0 |
| Scheme III | = | 44.65 | = | 100.0 |

Net heat input, as used in the above table, means the total amount of energy, expressed as MM Btu/hr, which must be expended to produce a given amount of product.

It can be seen that the practice of the present invention permits a substantial increase in the efficiency of energy use. Scheme I, which uses $C_9$ vapor injection directly into the column which produces a benzene product, requires 133.2% of the heat input of the present invention. Scheme II, the conventional peeling mode of fractionation requires 123.0% of the net heat input of the present invention.

In other embodiments, where, e.g., orthoxylene production is not of interest, the present invention may still be practiced by using a single xylene fractionator to separate $C_8$ alkylbenzene, from $C_9$ and heavier alkylaromatics. In this case only a portion of the $C_8$ alkylaromatic vapor fraction may be needed for the BT reboiler.

I claim as my invention:

1. A combination xylene separation and a toluene transalkylation process, for producing benzene and orthoxylene comprising the steps of:
   a. transalkylating a mixture of toluene and $C_9$ alkylbenzene in a transalkylation zone at transalkylation conditions to produce a transalkylation zone effluent comprising benzene, toluene, $C_8$ alkylbenzenes, $C_9$ alkylbenzenes, and $C_{10}$ alkylbenzenes;
   b. fractionating at least a portion of said transalkylation zone effluent in a distillation column wherein benzene and toluene are recovered as an overhead fraction and materials heavier than toluene are recovered as a bottoms fraction;
   c. fractionating said benzene and toluene fraction in a fractionation column to produce a benzene product and to recover a toluene-rich stream which comprises at least a portion of the charge to the transalkylation zone;
   d. passing at least a portion of said bottoms fraction, comprising material heavier than toluene, into a xylene fractionator, and recovering overhead a stream comprising orthoxylene and recovering as a bottoms fraction a stream comprising $C_9$ and $C_{10}$ alkylbenzenes;
   e. passing the $C_9$ and $C_{10}$ alkylbenzene bottoms fraction to a fractionation zone to recover overhead a stream comprising $C_9$ alkylbenzenes, at least a portion of which $C_9$ alkylbenzenes stream is charged to the transalkylation zone;
   f. reboiling the column producing benzene product by indirect heat exchange with vapors from the column producing $C_9$ alkylbenzenes as an overhead fraction; and,
   g. reboiling the column producing benzene and toluene as an overhead fraction by indirect heat exchange with a stream comprising orthoxylene vapors obtained as an overhead vapor fraction from the xylene fractionator.

2. Process of claim 1 wherein the xylene fractionator is a single fractionator, wherein $C_8$ alkylbenzenes, including orthoxylene, are recovered as an overhead vapor fraction and $C_9$ and heavier alkylbenzenes are recovered as a bottoms fraction.

3. Process of claim 1 wherein the xylene fractionator comprises two fractionators, a xylene splitter wherein meta- and para-xylene are recovered as an overhead fraction and orthoxylene and heavier alkylbenzenes recovered as a bottoms fraction are charged to an orthoxylene column wherein orthoxylene is recovered overhead as an overhead vapor fraction and $C_9$ and heavier alkylbenzenes are recovered as a bottoms fraction.

4. Process of claim 3 wherein the meta- and para-xylene overhead fraction is charged to an isomerization zone and at least a portion of the isomerization zone effluent is charged to the xylene splitter.

5. Process of claim 1 wherein the transalkylation zone effluent also contains alkylbenzenes heavier than $C_{10}$ and wherein the fractionator in step (e) recovers overhead a stream comprising $C_9$ and $C_{10}$ alkylbenzenes and recovers as a bottoms fraction a stream comprising alkylaromatics heavier than $C_{10}$.

* * * * *